United States Patent [19]

Runge

[11] 4,293,961

[45] Oct. 13, 1981

[54] PULSATILE FLOW CARDIOPULMONARY BYPASS PUMP

[76] Inventor: Thomas M. Runge, 2501 Galewood Pl., Austin, Tex. 78703

[21] Appl. No.: 134,089

[22] Filed: Mar. 26, 1980

[51] Int. Cl.[3] .................... A61F 1/00; A61B 19/00; F04B 43/00

[52] U.S. Cl. .................................. 3/1.7; 128/1 D; 74/57; 417/412

[58] Field of Search ............ 128/1 D, DIG. 3; 3/1.7; 417/412; 74/57

[56] References Cited

U.S. PATENT DOCUMENTS

| | | | |
|---|---|---|---|
| 314,469 | 3/1885 | Perkins et al. | 74/57 |
| 396,147 | 1/1889 | Monnin | 74/57 |
| 3,260,289 | 7/1966 | Whitten, Jr. | 74/57 X |
| 3,406,625 | 10/1968 | Chamness et al. | 74/57 X |
| 4,143,425 | 3/1979 | Runge | 417/412 X |

*Primary Examiner*—Gene Mancene
*Assistant Examiner*—Mickey Yu
*Attorney, Agent, or Firm*—B. P. Fishburne, Jr.

[57] ABSTRACT

A pulsatile flow cardiopulmonary bypass pump for use outside of the body during cardiac surgery and/or in the period immediately thereafter is disclosed. A grooved spinner is motor driven through a fluid coupling which enables idling of the spinner during diastole. The shell of the pump has a roof to which the spinner drive motor is attached, and the roof can move axially of the shell body and is biased resiliently in one axial direction. The roof of the shell moves as a function of duration of systole and magnitude of afterload, reducing stroke volume in the presence of high afterload. A groove rider having a friction reducing ball bearing drives a ring follower housing during rotation of the spinner. The groove rider is positively displaced from engagement with a holding magnet on the ring follower housing by relatively stationary camming element external to the spinner, and a camming part on the far end of the spinner positively displaces the groove rider from the driving groove of the spinner into engagement with the holding magnet at the end of systole. A rough ride of the groove rider along the spinner during diastole is avoided, and the groove rider is not dependent on spring action.

6 Claims, 8 Drawing Figures

PULSATILE FLOW CARDIOPULMONARY BYPASS PUMP

BACKGROUND OF THE INVENTION

This invention is an improvement on the device disclosed and claimed in prior U.S. Pat. No. 4,143,425, issued to Runge on Mar. 13, 1979.

This invention seeks to improve on the reliability, efficiency and smoothness of operation of the pumping mechanism in said prior patent in several important respects. Potentially, the groove rider in the prior patent is subject to a jerky or rough ride over the spiral groove of the spinner in its return toward the motor end of the spinner during diastole. Eventually, this rough ride could damage the engaging parts and cause jamming of the mechanism to create a serious safety hazard. This drawback is completely eliminated in the present invention through the provision of positive camming means on the spinner to displace the groove rider toward engagement with a holding magnet on the surrounding ring follower housing which holds the rider out of contact with the spinner during its travel toward the far end of the spinner during diastole. Another camming means near the far end of the spinner positively separates the groove rider from the holding magnet and positively cams the rider back into engagement with the spinner groove, thus assuring a more reliable operation of the vital parts which drivingly interconnect the spinner and the ring follower housing, which in turn operates the ejection plate in the manner disclosed in the above-referenced patent.

Another important feature of the present invention resides in the fitting of the groove rider with a ball bearing element producing a low friction ride in the shallow spinner groove, again improving the efficiency and reliability of the pump.

Another significant improvement resides in the use of a fluid coupling, namely a hydraulic, vaned, perforated clutch between the pancake motor and the spinner. In addition to providing a smooth drive for the spinner, the latter is able to idle during diastole while the magnetically held groove rider is traveling toward the motor end of the spinner.

A very important aspect of the present invention resides in the spring suspension of the roof of the shell to which the pancake motor is attached. By virtue of this arrangement, the shell roof can slide freely as a function of duration of systole and magnitude of after load, reducing stroke volume in the presence of high after load. Through the simple mechanical feedback means thus provided, the pump automatically adjusts its pumping rate in response to filling pressure, and automatically reduces its stroke volume in response to after load. These physiologic and safety features are not available in state of the art pumps.

While the present device is intended for use outside of the body during cardiac surgery and for longer term cardiac support, as for a day or two after surgery, it is intended not to limit the invention to such usage, and the pump could be used for implantation in the body in the manner disclosed in U.S. Pat. No. 4,143,425 in conjunction with a source of power external to the body.

Other features and advantages of the invention will become apparent during the course of the following detailed description.

DETAILED DESCRIPTION

Figure 1:
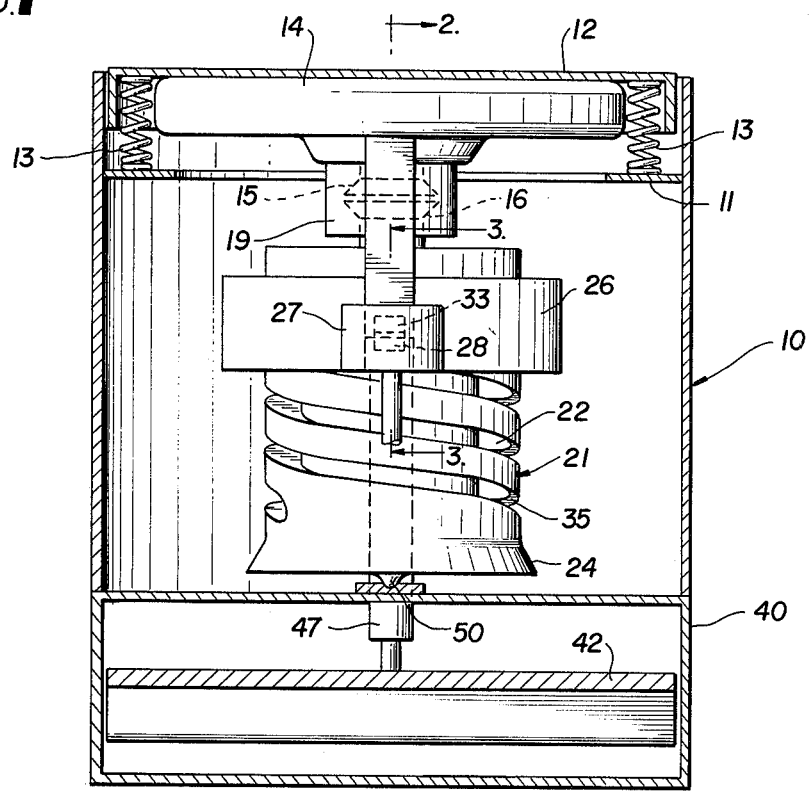
FIG. 1 is a central vertical section taken through a pulsatile flow pumping mechanism according to the invention.
Figure 2:
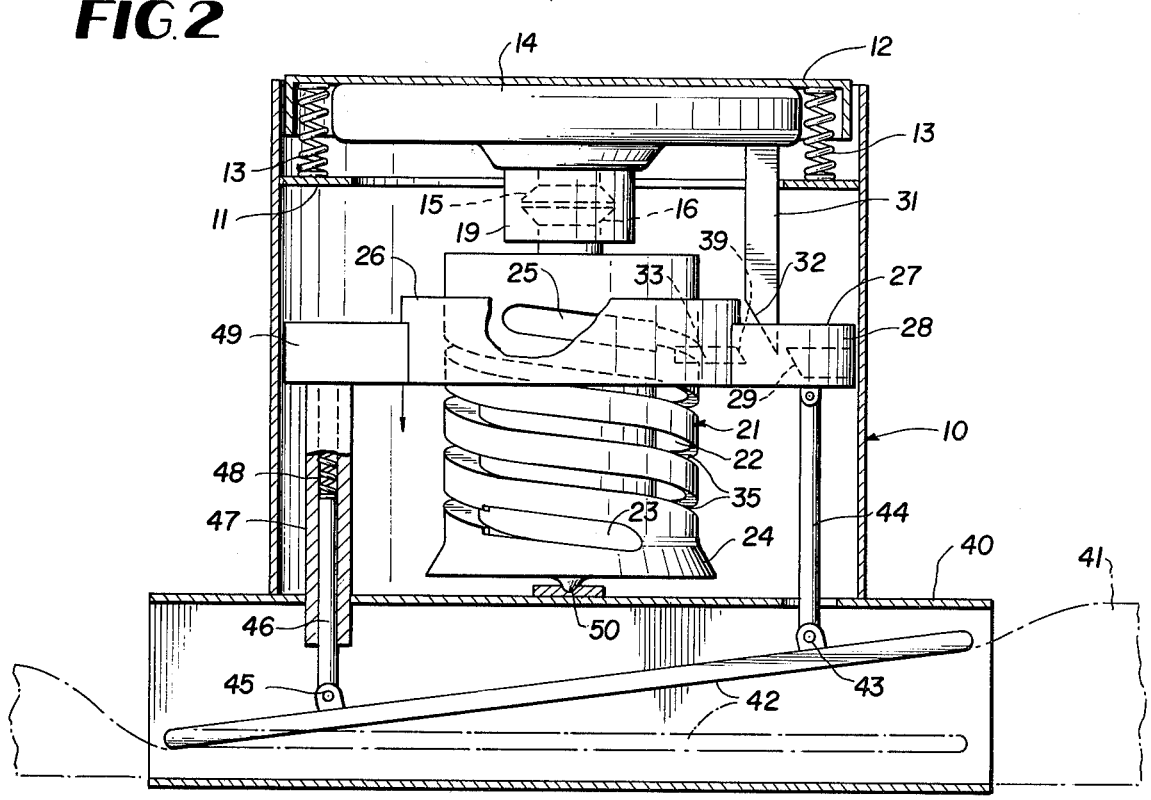
FIG. 2 is a central vertical section taken on line 2—2 of FIG. 1.

Referring to the drawings in detail wherein like numerals designate like parts, the numeral 10 designates a relatively stationary shell having an internal shelf ring 11 near one end thereof for the support of a shell roof 12 through a series of intervening compression springs 13 which yieldingly bias the roof 12 axially outwardly from the shelf ring 11.

Figure 6:
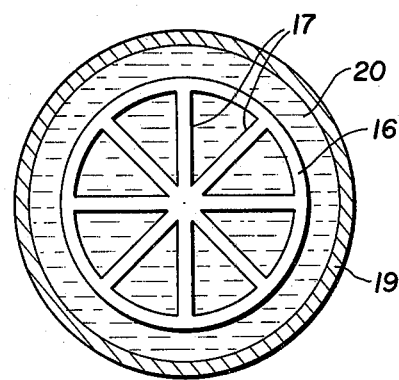
FIG. 6 is a horizontal section taken on line 6—6 of FIG. 5.

A pancake drive motor 14 of the type disclosed in prior U.S. Pat. No. 4,143,425 has its armature shaft directly coupled to the rotary driving element 15 of a hydraulic coupling or clutch having a companion driven element 16. The driving and driven hydraulic clutch elements 15 and 16 have radial vanes 17, shown schematically in FIG. 6, and the elements 15 and 16 rotate within a fixed enclosure 19 attached to the housing of motor 14 and therefore being non-rotatable. The enclosure 19 is filled with hydraulic fluid 20 through which torque is transmitted from the driving element 15 to the driven element 16 of the clutch or coupling.

The driven element 16 is attached to a spinner or rotor 21 which is broadly similar to the element 22 in U.S. Pat. No. 4,134,425. The spinner 21 has a shallow helical groove 22 including a widened exit portion 23 of gradually diminishing radial depth. The exit portion 23 extends to and terminates within a flared head 24 on one end of the spinner 21 for an important purpose to be described. Similarly, the far end of the spinner groove 22 has a widened entrance portion 25 leading into the spiral groove proper. Between the exit and entrance portions 23 and 25, the width of the groove 22 is restricted by an outer circumferential partial wall 35 which prevents the escape from the groove 22 of a groove rider 33 forming a key element of the invention to be described in further detail.

A ring follower housing 26 adapted to travel axially along the spinner 21 in two directions during rotation of the spinner surrounds the spinner and is held against rotation with the spinner. At one point on its circumference, the ring follower housing includes a first radial extension 27 containing a holding magnet 28 within a pocket 38 of the extension 27. The holding magnet 28 has a beveled inner face 29. The extension 27 has a through passage 30 parallel to the spinner axis which is adapted to receive a fixed groove rider separating cam 31 having a beveled end face 32. The cam 31 is attached dependingly to the housing of pancake motor 14 near the periphery thereof.

The groove rider 33 extends radially of the spinner 21 and is equipped near its inner end with a friction reducing ball bearing 34 projecting above the top of the rider 33 to engage the top wall of spiral groove 22 which is exerting downward pressure on the rider during rotation to drive the rider downwardly with the ring follower housing 26.

Between the widened exit and entrance portions 23 and 25 the interior end of the rider 33 and its ball bearing 34 cannot escape from the spiral groove 22 because of the partial wall 35, as stated. However, the exit and entrance portions 23 and 25 are sufficiently wide to allow free passage of the rider and its ball bearing in the radial direction, at proper times, and the retaining partial wall 35 is absent at these regions.

Figure 4:
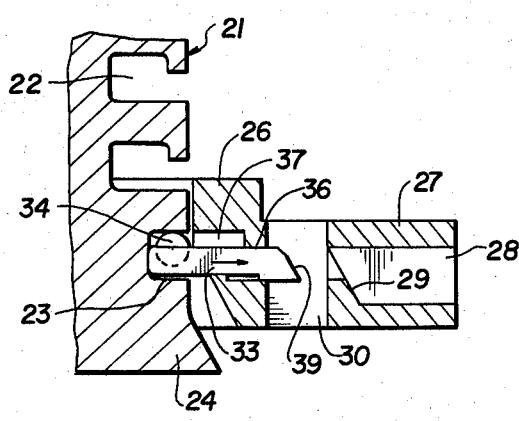
FIG. 4 is a similar view showing the groove rider and associated elements at the time of camming the rider away from the spinner and into contact with a holding magnet.
Figure 4A:
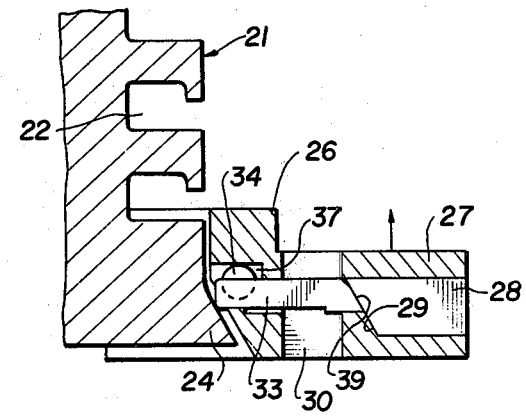
FIG. 4A is a similar view showing the groove rider, holding magnet and associated elements as the rider is beginning its return travel separated from the spinner during diastole.
Figure 5:
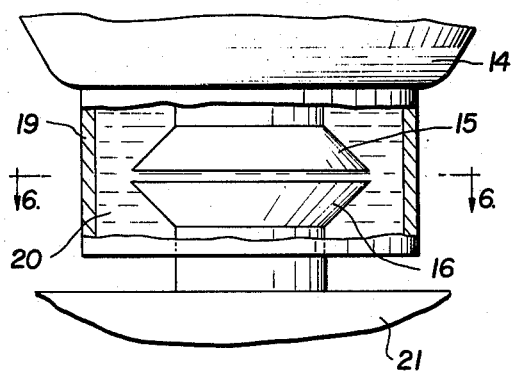
FIG. 5 is an enlarged fragmentary partly cross sectional and partly diagrammatic view of a fluid coupling between the pancake motor and spinner.

Since the exit portion 23 of the spiral groove runs out onto the flared head 24 of the spinner, a camming surface is formed near the adjacent end of the spinner which engages the rider 33 after it emerges from the retaining portion of groove 22 and gradually forces it radially outwardly toward the position shown in FIG. 4A where the rider 33 is completely separated from the spinner 21 and is in contact with the holding magnet 28. To facilitate this, the ring follower housing 26 has a radial guide passage 36 for the groove rider 33 including an inner end enlargement 37 to accommodate the ball bearing 34. The guide passage 36 intersects the through passage 30 and opens into the chamber 38 containing the magnet 28. The outer end face 39 of rider 33 is beveled in parallelism with the magnet end face 29.

As in U.S. Pat. No. 4,143,425, a compression chamber 40 is attached to the shell 10 and receives therethrough a Dacron shunt extending between the left atrium, not shown, and the descending thoracic aorta, not shown. Beyond opposite ends of the chamber 40, the compressible shunt 41 is equipped with a pair of porcine valves as shown in the referenced patent. An ejection plate 42 has one end pivotally coupled at 43 with a solid leg 44 whose other end is attached to the extension 27 of ring follower housing 26. At a second point, the ejection plate 42 is pivotally coupled at 45 to a lost motion pin 46 slidable in the bore of a tubular leg 47 containing an outwardly biasing spring 48 for the pin 46. The tubular leg 47 is attached to a second radial extension 49 on follower ring housing 26 diametrically opposite the extension 27. A center point bearing 50 for the spinner 21 is provided as shown.

OPERATION

Motor 14, through fluid coupling 15-16, rotates spinner 21 in the direction whereby spiral groove 22 drives groove rider 33 away from the motor 14 and toward the flared head 24 of the spinner.

Figure 3:
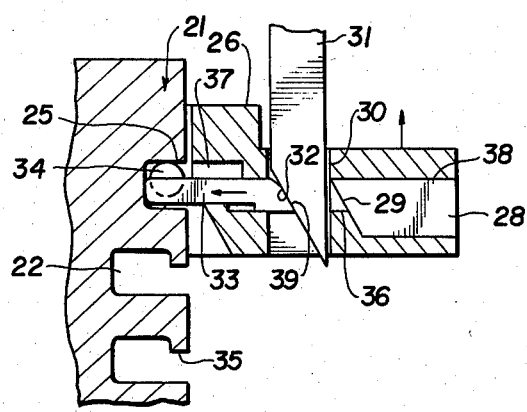
FIG. 3 is an enlarged fragmentary vertical section showing the relationship between a groove rider and rider displacement cam when the rider is being moved into the groove of a spinner.
Figure 3A:
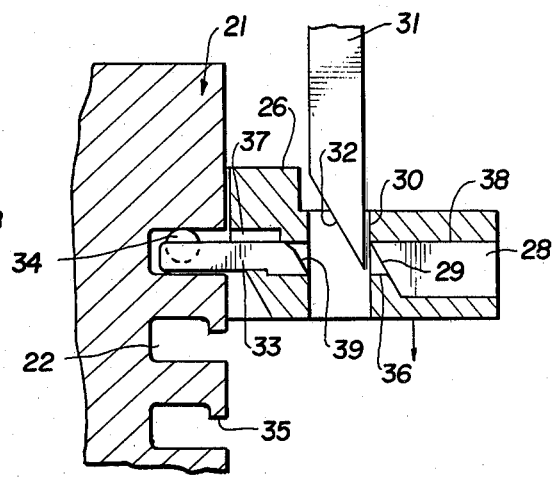
FIG. 3A is a similar view showing the relationship of the rider to the spinner and relatively stationary camming means as the rider begins to be driven in one direction along the axis of the spinner.

Assuming that the groove rider is at some intermediate location in the groove 22 between entrance and exit portions 25 and 23, FIG. 3A, the partial wall 35 will prevent the groove rider from moving radially outwardly toward the separated position of FIG. 4A. Also, the driving pressure of the spinner on the rider will be at the point of contact of ball bearing 34 with the top wall of spiral groove 22.

Upon reaching the vicinity of the groove exit portion 23 of increased width, the partial wall 35 is interrupted, and the exit portion 23 becomes progressively shallower as the exit portion fades into the flared head 24 to form a camming surface which extends radially beyond the periphery of the spinner 21. During continued rotation of the spinner, this camming surface acts on the rear of groove rider 33 and displaces it radially outwardly to the position of FIG. 4A. During such movement of the groove rider, it is accurately guided by the passage 36 and the passage enlargement 37 receives the ball bearing 34. The rider 33 is now totally outside of the spinner 21 and its outer beveled face 39 is in contact with the face 29 of magnet 28 and held in such contact by magnetic attraction. This condition comes into being at the end of systole.

At the commencement of diastole, the ring follower housing 26 begins to travel in the reverse direction along the rotating spinner 21 or toward the motor 14. Because of the fluid drive coupling 15-16, the spinner can idle during diastole. Since the rider 33 is beyond the periphery of the spinner 21, there is no contact between the rider and the spiral groove 22 during the return travel of the rider with the ring follower housing 26 as could occur in the prior art.

Near the end of diastole, FIG. 3, the steeply beveled surface 32 of fixed cam 31 enters the through passage 30 and begins to engage the beveled end face 39 of the rider 33, and this forces the groove rider radially inwardly toward the position shown in FIG. 3A. The ball bearing 34 leaves the enlargement 37 and the inner end of the rider with the ball bearing enters the entrance portion 25 of the spinner groove. While the cam surface 32 is still acting on the rider 33, the ball bearing and rider will pass into the retaining portion of the groove 22 having the partial wall 35 and the rider with the ring follower housing 26 will again be positively driven away from the motor 14 and toward the compression chamber 40. The cycle of operation as described is continuously repetitive as long as the motor is running. In both directions of displacement, the groove rider 33 is positively cam operated and not dependent upon spring action. The operation of the mechanism in its entirety is characterized by precision and smoothness with minimal friction and wear.

The operation of the ejection plate 42 on the compressible valved shunt 41 is exactly the same as described in U.S. Pat. No. 4,143,425.

Because of the simple mechanical feedback arrangement through springs 13 and moving roof 12, the pump automatically adjusts its pumping rate in response to filling pressure in the shunt 41, and automatically reduces its stroke volume in response to afterload. Thus the mechanism closely resembles the physiology of the natural heart.

it is to be understood that the form of the invention herewith shown and described is to be taken as a preferred example of the same, and that various changes in the shape, size and arrangement of parts may be resorted to, without departing from the spirit of the invention or scope of the subjoined claims.

I claim:

1. A pulsatile flow pumping mechanism particularly adapted to operate a cardiopulmonary bypass device comprising a rotary spinner having a spiral groove including a partial retainer wall and entrance and exit groove portions of increased width and progressively decreasing depth beyond the terminals of the partial retainer wall, power drive means connected with the spinner to rotate it in one direction, a ring follower housing surrounding the spinner and operatively coupled with said bypass device and adapted to traverse the spinner axially of the spinner and being held against rotation with the spinner, a holding magnet on the ring follower housing radially outwardly of the spinner, a magnetically attractable groove rider mounted for movement radially of the spinner within a passage of the ring follower housing which is in alignment with said magnet, camming surface means on the spinner near one end thereof including the exit groove portion of the spinner engageable with said rider to displace the rider radially outwardly into held engagement with said magnet with the rider radially beyond the periphery of the spinner, and stationary cam means near the opposite end of the spinner and radially outwardly of the periphery of the spinner to strip said rider from the holding magnet and move it into said entrance groove portion.

2. A pulsatile flow pumping mechanism as defined in claim 1, and said power drive means comprising a drive motor for the spinner and a fluid torque transmitting device operatively coupled between said drive motor and spinner.

3. A pulsatile flow pumping mechanism as defined in claim 2, and a shell for the pumping mechanism including an axially movable shell roof attached to said drive motor, and resilient biasing means for said roof connected between the roof and said shell.

4. A pulsatile flow pumping mechanism as defined in claim 1, and a ball bearing on said groove rider having driven contact with the top wall of said spiral groove and serving as a retainer element for the groove rider through opposing relationship with said partial retainer wall.

5. A pulsatile flow pumping mechanism as defined in claim 1, and said holding magnet and groove rider having opposing inclined end faces, said stationary cam means having a tapered tip including an inclined end face operable to wedge said rider away from the holding magnet and to cam the rider radially inwardly toward said entrance groove portion.

6. A pulsatile flow pumping mechanism as defined in claim 1, and said camming surface means on the spinner comprising a flared enlargement on the spinner near said one end projecting outwardly of the periphery of the spinner, the exit groove portion extending to and terminating within said flared enlargement to form a camming surface radially beyond the periphery of the spinner for displacing said rider radially outwardly beyond the periphery of the spinner and into held engagement with the magnet.

* * * * *